United States Patent [19]
Muraoka et al.

[11] Patent Number: 6,132,761
[45] Date of Patent: Oct. 17, 2000

[54] PERCUTANEOUS ABSORPTION PREPARATION

[75] Inventors: Takateru Muraoka; Hitoshi Akemi; Keigo Inosaka; Hiroko Ishitani; Saburo Otsuka, all of Osaka, Japan

[73] Assignee: Nitto Denko Corporation, Osaka, Japan

[21] Appl. No.: 09/146,666

[22] Filed: Sep. 3, 1998

[30] Foreign Application Priority Data

| Sep. 5, 1997 | [JP] | Japan | 9-240779 |
| Sep. 5, 1997 | [JP] | Japan | 9-240780 |
| Sep. 5, 1997 | [JP] | Japan | 9-241435 |

[51] Int. Cl.$^7$ ............................................... A61F 13/02
[52] U.S. Cl. ................................................ 424/448
[58] Field of Search ........................................... 424/448

[56] References Cited

FOREIGN PATENT DOCUMENTS 0 268 219 A1   5/1988   European Pat. Off. .
0 280 737 A1   9/1988   European Pat. Off. .

OTHER PUBLICATIONS

Sokolowska, Regina, Identification of Antioxidants Used for Polyethylene, Rocz. Panstw, Zakl. Hig., (1966), 17(5), pp. 439–446.

Ninomiya, Kazuhisa, et al., Transdermal Tapes Containing Polymeric Base with Pharmaceuticals and Their Stabilizer, Propyl Gallate, Jpn. Kokai Tokkyo Koho, 7pp, Jun. 1987.

Kale, P. et al., "Preformulation Stability and Permeation Studies of Transdermal Patches of Salbutamol," *Indian Journal of Pharmaceutical Sciences*, Sep.–Oct. 1996, pp. 211–215.

Kenji, H., "Composition for Heat–Resistant Self–Welding Crosslinked Polyolefin Tape," *Patent Abstracts of Japan*, Oct. 27, 1983.

Akira, M., "Adhesive Tape," *Patent Abstracts of Japan*, Oct. 11, 1980.

Akemi, H., et al., "Percutaneous agent contain mercapto benzimidazole stabilized amino chloro isopropyl methyl piperazinyl benzimidazole adhesive layer control side effect chemotherapy," Japanese Abstract, 1997.

Ninomiya, K., et al., "Transdermal tapes containing polymeric base with pharmaceuticals and their stabilizer, propyl gallate," Japanese Abstract, 1988.

*Primary Examiner*—Jose' G. Dees
*Assistant Examiner*—Michael A. Williamson
*Attorney, Agent, or Firm*—McGuire Woods

[57] ABSTRACT

The present invention provides a percutaneous absorption preparation which hardly causes the coloration phenomenon and is excellent in the stability of the drug content. The percutaneous absorption preparation comprises a support and a pressure-sensitive adhesive layer formed on at least one side of the support, wherein the pressure-sensitive adhesive layer contains a percutaneous absorptive drug and at least one of 2-mercaptobenzimidazole and propyl gallate, with the proviso that the percutaneous absorptive drug is not 6-amino-5-chloro-1-isopropyl-2-(4-methyl-1-piperazinyl) benzimidazole and pharmacologically acceptable salt thereof.

6 Claims, No Drawings

PERCUTANEOUS ABSORPTION PREPARATION

FIELD OF THE INVENTION

The present invention relates to a percutaneous absorption preparation, more specifically, a percutaneous absorption preparation which enables stable existence of a percutaneously absorptive drug in the preparation and in particular, is suppressed in the coloration and excellent in stability of the drug content.

BACKGROUND OF THE INVENTION

As a percutaneous absorption preparation for the administration of a drug to a living body through the skin surface, various external preparations used by being patched to the skin surface such as cataplasm or medical tape have been developed. Among such preparations, a medical tape having a drug, which exhibits systemic pharmacological effects, contained therein has particularly attracted attentions. Under such situations, tape-shaped percutaneous absorption preparations each having a pharmacologically active substance, such as nitroglycerin, isosorbide nitrate, steroid preparation, non-steroid preparation, anesthesia or antihypertensive drug, incorporated in a pressure-sensitive adhesive has been proposed and developed. Some of them have already been put on the market.

Such percutaneous absorption preparations are each prepared by incorporating a percutaneously absorptive drug in an acrylic or synthetic rubber series pressure-sensitive adhesive. Only by the application of it to the skin, the drug is absorbed continuously in a living body and then exhibits excellent pharmacological action.

Since they have a percutaneously absorptive drug incorporated in a pressure-sensitive adhesive, however, a decomposition product appears as a result of the interaction between various trace components in the pressure-sensitive adhesive and the drug, whereby the resulting percutaneous absorption preparation is colored. In addition, the colored degree of many preparations tends to be heightened during the storage of the preparation.

In general, the reaction of a drug with the component in a pressure-sensitive adhesive produces a decomposition product so that it is the common practice to reveal the structure of the decomposition product and then add a decomposition inhibitor (antioxidant, stabilizer or the like) to prevent the decomposition. With regards to the coloration phenomenon, most of the reaction products of a trace component cause so much coloring as to exceed the permissible limit of the appearance of the preparation and it is considerably difficult to investigate means for preventing such coloring.

As a matter of fact, therefore, it is generally inevitable to depend on time-spending and inefficient means for screening a proper compound, more specifically, to add a large number of compounds to a preparation respectively and select a proper compound which does not cause coloring of the preparation.

SUMMARY OF THE INVENTION

An object of the present invention is to provide a percutaneous absorption preparation which is suppressed in the coloration phenomenon, which occurs upon incorporation of a percutaneously absorptive drug in a pressure-sensitive adhesive, thereby having a permissible level of appearance and is excellent in the stability of the drug content.

With a view toward overcoming the above-described problems, the present inventors have carried out an extensive investigation. As a result, it has been found that a stable percutaneous absorption preparation suppressed both in the coloration, which is caused by the interaction between a percutaneous absorptive drug and a trace component in a pressure-sensitive adhesive, and in the heightening of the colored degree during the storage time can be obtained by incorporating, in the pressure-sensitive adhesive layer, 2-mercaptobenzimidazole and/or propyl gallate together with the percutaneous absorptive drug, with the proviso that the percutaneous absorptive drug is not 6-amino-5-chloro-1-isopropyl-2-isopropyl-2-(4-methyl-1-piperazinyl)benzimidazole and a pharmaceutically acceptable salt thereof.

The present invention will be summarized as follows:

(1) A percutaneous absorption preparation which comprises a support and a pressure-sensitive adhesive layer formed on at least one side of the support, wherein the pressure-sensitive adhesive layer contains a percutaneous absorptive drug and at least one of 2-mercaptobenzimidazole and propyl gallate, with the proviso that the percutaneous absorptive drug is not 6-amino-5-chloro-1-isopropyl-2-(4-methyl-1-piperazinyl)benzimidazole and pharmacologically acceptable salt thereof.

(2) A percutaneous absorption preparation as described in (1) wherein said pressure-sensitive adhesive layer is formed of a non-functional pressure-sensitive adhesive.

(3) A percutaneous absorption preparation as described in (2), wherein said non-functional pressure-sensitive adhesive is at least one pressure-sensitive adhesive selected from the group consisting of pressure-sensitive adhesives made of an acrylic polymer, rubber pressure-sensitive adhesives, silicone pressure-sensitive adhesives, vinyl ether pressure-sensitive adhesives and vinyl ester pressure-sensitive adhesives.

(4) A percutaneous absorption preparation as described in (1), wherein said pressure-sensitive adhesive layer comprises an acrylic polymer obtained by copolymerization of a functional monomer as an essential component.

(5) A percutaneous absorption preparation as described in (4), wherein an azo compound is employed as a polymerization initiator upon copolymerization to obtain the acrylic polymer.

(6) A percutaneous absorption preparation as described in (4), wherein an organic peroxide compound is used as a polymerization initiator upon copolymerization to obtain the acrylic polymer.

The percutaneous absorption preparation according to the present invention has a pressure-sensitive adhesive layer, which contains a pressure-sensitive adhesive, a percutaneous absorptive drug and 2-mercaptobenzimidazole and/or propyl gallate, formed on at least one side of a support and prevents the coloration phenomenon which occurs upon incorporation of the percutaneous absorptive drug in the pressure-sensitive adhesive layer. The use of a non-functional pressure-sensitive adhesive does not require any polymerization initiator. When an acrylic copolymer obtained by the copolymerization of a functional monomer as an essential component is employed, however, the use of an azo compound or organic peroxide compound as a polymerization initiator upon copolymerization is effective for the prevention of a coloration phenomenon. Accordingly, the present invention makes it possible to provide a stable preparation which is suppressed in both a coloration phenomenon due to the interaction between the percutaneous absorptive drug and various trace components in the pressure-sensitive adhesive and a heightening phenomenon of the colored degree during the storage time so as to maintain a pharmaceutically acceptable appearance. In addition, the percutaneous absorption preparation according to the present invention is excellent in the stability of the content of its percutaneous absorptive drug.

DETAILED DESCRIPTION OF THE INVENTION

Although no particular limitation is imposed on the support usable for the percutaneous absorption preparation of the present invention, it is preferred to use a support which does not allow the percutaneous absorptive drug, 2-mercaptobenzimidazole and/or propyl gallate and additives such as plasticizer or absorption enhancer to pass through it, to be lost from another side of it, and therefore to cause a content reduction, in short, a support which is formed of a material through which no transmission of such components occurs.

Specific examples include a single film or laminate film of polyesters such as polyethylene terephthalate, polyamides such as nylon, polyolefins such as polyethylene and polypropylene, polyvinyl chloride, plasticized polyvinyl chloride, plasticized vinyl acetate-vinyl chloride copolymer, polyvinylidene chloride, ethylene-vinyl acetate copolymer, cellulose acetate, ethyl cellulose, ethylene-ethyl acrylate copolymer, polytetrafluoroethylene, polyurethane, ionomer resins and metallic foils such as aluminum foil. The supports having flexibility are preferred.

The support can have such a thickness that the soft feeling of the percutaneous absorption preparation is not impaired, generally a thickness of from 1 to 25 $\mu$m, preferably from 1 to 15 $\mu$m.

It is preferred that in order to improve the anchoring property (adhesion) between the support and the pressure-sensitive adhesive layer, particularly in the percutaneous absorption preparation having an additive such as plasticizer or absorption enhancer incorporated therein, the support takes the form of a laminate with a porous film, with the pressure-sensitive adhesive layer being formed on the side of the porous film.

Specific examples of the porous film include paper, woven cloth, non-woven cloth and mechanically perforated film.

In consideration of the improvement in the anchoring property and the flexibility of the whole percutaneous absorption preparation, the porous film is preferred to have a thickness of 10 to 500 $\mu$m, while it is preferred to have a thickness falling within a range of 10 to 200 $\mu$m in the case of a thin preparation such as plaster or pressure-sensitive adhesive tape type preparation.

When a woven cloth or non-woven cloth is used as the porous film, the coat weight of the pressure-sensitive adhesive layer is desired to set at 5 to 30 g/m$^2$, preferably 8 to 20 g/m$^2$ from the viewpoint of the improvement of the anchoring property. It is also possible to use a relatively air-permeable material as the support in order to suppress the drug releasability of the percutaneous absorption preparation.

The percutaneous absorption preparation has a pressure-sensitive adhesive layer, which will be described later, formed on at least one side of the above-described support.

The pressure-sensitive adhesive layer is prepared by incorporating a percutaneous absorptive drug other than 6-amino-5-chloro-1-isopropyl-2-(4-methyl-1-piperazinyl) benzimidazole and pharmacologically acceptable salt thereof, 2-mercaptobenzimidazole and/or propyl gallate in a pressure-sensitive adhesive and then forming the resulting mixture as a layer.

As a pressure-sensitive adhesive to be used for the pressure-sensitive adhesive layer of the present invention, it is preferred to adopt a pressure-sensitive adhesive which has, not only a function of sticking and fixing the percutaneous absorption preparation closely to the skin surface, thereby releasing the percutaneous absorptive drug contained therein to the skin surface, but also a function of preventing decomposition of the percutaneous absorptive drug as much as possible and maintaining the drug stably, thereby suppressing the coloration of the pressure-sensitive adhesive layer or deterioration of the coloration during the storage time.

As such a pressure-sensitive adhesive, a non-functional pressure-sensitive adhesive having no functional group is effective. The term "non-functional pressure-sensitive adhesive" as used herein means a pressure-sensitive adhesive which substantially has neither polar functional group such as —OH, —COOH or —NH$_2$ nor reactive unsaturated bond at an end of the molecule constituting the pressure-sensitive adhesive. Described specifically, it means a pressure-sensitive adhesive having a functional group which does not substantially take part in the copolymerization, i.e., a pressure-sensitive adhesive not having any functional group which substantially takes part in the copolymerization.

Specific examples of the non-functional pressure-sensitive adhesive include pressure-sensitive adhesives composed of an acrylic polymer available by the copolymerization of an alkyl acrylate and/or methacrylate ("acrylate and/or methacrylate" may hereinafter be called "(meth)acrylate"), and/or alkoxy-modified monomer thereof; rubber pressure-sensitive adhesives composed of polyisoprene, polyisobutylene, polybutadiene, styrene-butadiene-block copolymer and styrene-isoprene-styrene block copolymer; silicone pressure-sensitive adhesives such as silicone rubber and dimethyl siloxane base pressure-sensitive adhesive and diphenyl siloxane base pressure-sensitive adhesive; vinyl ether pressure-sensitive adhesives composed of polyvinylmethyl ether, polyvinylethyl ether or polyvinylisobutyl ether; vinyl ester pressure-sensitive adhesives composed of vinyl acetate-ethylene copolymer; and polyester pressure-sensitive adhesives composed of a carboxylic acid component such as dimethyl terephthalate, dimethyl isophthalate or dimethyl phthalate and a polyhydric alcohol component such as ethylene glycol. Preferably, at least one pressure-sensitive adhesive selected from the group consisting of pressure-sensitive adhesives composed of an acrylic copolymer, rubber pressure-sensitive adhesives, silicone pressure-sensitive adhesives, vinyl ether pressure-sensitive adhesives and vinyl ester pressure-sensitive adhesives is employed.

Among them, pressure-sensitive adhesives composed of an acrylic polymer and rubber, silicone and vinyl ester pressure-sensitive adhesives are preferred from the viewpoints of adhesion to the skin, drug solubility and drug stability, with the acrylic polymer type, rubber type such as polyisobutylene and styrene-isoprene (or butadiene)-styrene block copolymer and silicone type being more preferred.

The above-described acrylic polymer can be obtained by polymerizing an alkyl (meth)acrylate and/or alkoxy-modified monomer of an alkyl (meth)acrylate as a main component. The alkyl (meth)acrylate is desired to contain, as its alkyl group, a linear or branched alkyl group having 4 to 13 carbon atoms from the viewpoint of the adhesion to the skin. The acrylic polymer obtained by using one or more of such monomers in a total amount of not less than 50 wt. % is preferred.

The term "alkoxy-modified monomer of an alkyl (meth) acrylate" as used herein means an alkyl (meth)acrylate having an alkyl group modified with a linear or branched alkoxy group having 1 to 10 carbon atoms (e.g., methoxy, ethoxy, methoxyethylene glycol, or methoxypolyethylene glycol). Specific examples include methoxyethyl (meth) acrylate, ethoxyethyl (meth)acrylate, methoxyethylene glycol (meth)acrylate and methoxypolyethylene glycol (meth) acrylate. Such a monomer is preferred to be used for the copolymerization with the alkyl (meth)acrylate in an amount within a range not exceeding 50 wt. % from the viewpoints of adhesion to the skin and solubility and stability of a drug.

In addition to the above-described monomers, it is also possible to add a monomer such as styrene, phenyl (meth) acrylate, alkyl (meth)acrylate containing a linear or branched alkyl group having three or less carbon atoms [e.g., methyl (meth)acrylate, ethyl (meth)acrylate and propyl (meth)acrylate] or vinyl acetate upon copolymerization so as to improve the cohesiveness of the pressure-sensitive adhesive.

The non-functional pressure-sensitive adhesive may contain one or more known additives such as tackifier (e.g., rosin, modified rosin, petroleum resin, polyterpene resin, polystyrene resin, polybutene resin or liquid polyisobutylene), plasticizer (e.g., liquid paraffin), absorption enhancer, surfactant or filler, as desired, to further improve the pressure-sensitive adhesion.

As well as the above-described non-functional pressure-sensitive adhesive, an acrylic copolymer obtained by the copolymerization of a functional monomer as an essential component can also be used as the pressure-sensitive adhesive of the present invention. Having a functional group, this copolymer is advantageous from the viewpoints of releasability of the drug and reactivity upon crosslinking treatment. However, it possibly accelerates decomposition of the percutaneous absorptive drug compared with the above-described acrylic copolymer obtained from a non-functional monomer. Accordingly, an azo compound or organic peroxide compound is used as a polymerization initiator upon copolymerization.

The pressure-sensitive adhesive formed of the above-described acrylic copolymer can be obtained by copolymerizing an alkyl (meth)acrylate, which is used for an ordinary acrylic pressure-sensitive adhesive, as a main component monomer and a functional monomer.

The alkyl (meth)acrylate is desired to contain, as its alkyl group, the above-described linear or branched, alkyl group having 4 to 13 carbon atoms from the viewpoint of adhesion to the skin. Examples of such an alkyl group include butyl, pentyl, hexyl, heptyl, octyl, nonyl, decyl, undecyl, dodecyl and tridecyl. Incidentally, the alkyl (meth)acrylate is not limited to those as exemplified above, but it is possible to use an alkyl (meth)acrylate having an alkyl group having 1 to 3 carbon atoms or that having an alkyl group containing at least 14 carbon atoms in combination within an extent not causing a change in the characteristics of the present invention.

As the functional monomer, that having in its molecule at least one unsaturated double bond which takes part in the copolymerization and at the same time having a functional group at its side chain can be used. Examples of such a functional monomer include carboxyl-containing monomers such as (meth)acrylic acid, itaconic acid, maleic acid and maleic anhydride; hydroxyl-containing monomers such as hydroxyethyl (meth)acrylate and hydroxypropyl (meth) acrylate; sulfoxyl-containing monomers such as styrenesulfonic acid, allylsulfonic acid, sulfopropyl (meth)acrylate, (meth)acryloyloxynaphthalenesulfonic acid and acrylamidomethylpropanesulfonic acid; amino-containing monomers such as aminoethyl (meth)acrylate, dimethylaminoethyl (meth)acrylate and tert-butylaminoethyl (meth)acrylate; amide-containing monomers such as (meth)acrylamide, n-methylol (meth)acrylamide and N-methylolpropane (meth)acrylamide; and alkoxy-containing monomers such as methoxyethyl (meth)acrylate, ethoxyethyl (meth)acrylate, methoxyethyleneglycol (meth)acrylate, methoxydiethyleneglycol (meth)acrylate, methoxypolyethylene glycol (meth)acrylate, methoxypolypropyrene glycol (meth) acrylate and tetrahydrofurfuryl (meth)acrylate.

Examples of a copolymerizable monomer other than the above monomers include (meth)acrylonitrile, vinyl acetate, vinyl propionate, N-vinyl-2-pyrrolidone, methylvinylpyrrolidone, vinylpyridine, vinylpiperidone, vinyl pyrimidine, vinyl piperazine, vinylpyrazine, vinylpyrrole, vinyl imidazole, vinylcaprolactam, vinyloxazole and vinylmorpholine.

The above-exemplified functional monomers can be copolymerized either singly or in combination. It is particularly preferred to copolymerize at least one carboxyl-containing monomer or hydroxyl-containing monomer as an essential component and optionally the above-exemplified monomer, in consideration of pressure-adhesion properties such as adhesion and cohesiveness, releasability of a percutaneous absorptive drug contained in the pressure-sensitive adhesive layer and reactivity of the pressure-sensitive adhesive upon the crosslinking treatment. The amount of the above-described functional monomer can be determined generally in the range of 2 to 40 wt. %, preferably from 3 to 35 wt. % of the total amount of the monomers depending on the purpose.

In the present invention, when an acrylic copolymer obtained by the copolymerization of a functional monomer as an essential component is used as a pressure-sensitive adhesive, it is desired to use an azo compound or organic peroxide compound as a polymerization initiator from the viewpoints of the easiness of the polymerization reaction and physical properties of the pressure-sensitive adhesive obtained from the acrylic copolymer.

Specific examples of such an azo compound include azo and diazo compounds, for example, azobisnitrile compounds such as azobisisobutylonitrile, azobispropionitrile and azobisvaleronitrile, diazoaminobenzene, nitrosoacylallylamines, azothioethers and p-nitrobenzene diazonium salt.

Specific examples of the organic peroxide compound include benzoyl peroxide, lauroyl peroxide, acetyl peroxide, ketone peroxide, cumene hydroperoxide, t-butyl hydroperoxide and di-t-butyl peroxide.

Upon copolymerization, the polymerization initiator can be added generally in an amount of 0.01 to 2 parts by weight, preferably 0.05 to 2 parts by weight based on 100 parts by weight of the total amount of the monomers.

In the present invention, the pressure-sensitive adhesive formed of an acrylic copolymer can be obtained by synthesizing the above-described monomer, which is a main component, and a functional monomer in the presence of the above-described polymerization initiator according to the conventionally known method. Examples of the usable polymerization method include solution polymerization, emulsion polymerization, bulk polymerization and suspension polymerization. The pressure-sensitive adhesive may be subjected to crosslinking treatment as needed by the conventionally known method. The acrylic copolymer preferably has a weight-average molecular weight of 500,000 to 2,500,000.

The percutaneous absorption preparation according to the present invention can be prepared as an adhesive preparation intended for the treatment and/or prevention of various diseases by incorporating a percutaneous absorptive drug in a pressure-sensitive adhesive layer in the dissolved form or the dispersed solid form.

From the percutaneous absorptive drugs to be contained in the pressure-sensitive adhesive layer in the present invention, 6-amino-5-chloro-1-isopropyl-2-(4-methyl-1-piperazinyl)benzimidazole and pharmacologically acceptable salts thereof (e.g., hydrochloride, sulfate, maleate and fumarate) are excluded. The present inventors have found that to their surprise, 2-mercaptobenzimidazole and/or propyl gallate exhibits effects for stability and coloration prevention, irrespective of the kind of the drug, when incorporated in the pressure-sensitive adhesive. No particular limitation is therefore imposed on the kind of the drug insofar as it is absorbed percutaneously. Examples of the percutaneous absorptive drug include fat soluble drugs having a molecular weight not greater than 400, melting point not higher than 300° C. and water solubility not higher than 4 mg/ml. As the percutaneous absorptive drug, corticosteroid, anti-inflammatory analgesic, hypnotic analgesic, tranquilizer, antihypertensive, hypotensive diuretic, antibiotic, anesthesia, antibacterial agent, antimycotic, vitamin preparation, coronary vasodilator, antihistaminic, antitussive, sex hormone preparation, antidepressant, cerebral circulation improver, antiemetic, antitumor agent, biomedicine can be given as examples.

Specific examples include carboxylic acid derivatives, amino acid derivatives, amine derivatives, amidic acid derivatives, steroid derivatives, alcohol derivatives, aromatic amine derivatives, naphthalene derivatives and heterocyclic derivatives containing at least one hetero atom selected from the group consisting of oxygen, sulfur and nitrogen atoms. Preferred are heterocyclic derivatives containing at least one hetero atom selected from the group consisting of oxygen, sulfur and nitrogen atoms.

More specifically, examples include azelastine, verapamil, metoprolol, sodium valproate, L-methionine, meprobamate, estradiol, propranolol, pilocarpine, indomethacin, pindolol, nifedipine, ifenprodil, diazepam, clemizole and allopurinol. These drugs can be used in combination as needed.

The amount of such a drug can be determined as needed according to the kind of the drug or administration purpose. It is generally added in an amount of about 1 to 40 wt. %, preferably 2 to 30 wt. % to the pressure-sensitive adhesive layer. When the content is less than 1 wt. %, the amount of the drug released from the preparation tends to be insufficient and effects for the treatment or prevention cannot be expected. When the content exceeds 40 wt. %, on the other hand, treatment or prevention effects reach a saturated level, which is economically disadvantageous.

2-Mercaptobenzimidazole and/or propyl gallate incorporated, together with the above-described percutaneous absorptive drug, in the pressure-sensitive adhesive layer of the percutaneous absorption preparation of the present invention is presumed to act on trace components in the pressure-sensitive adhesive layer which will otherwise cause coloring by the interaction (oxidative decomposition, photolysis, hydrolysis) with the percutaneous absorptive drug, thereby inhibiting the reaction between the percutaneous absorptive drug and the trace components in the pressure-sensitive adhesive layer. This makes it possible to have the percutaneous absorptive drug exist stably in the preparation and to suppress both the coloration due to the interaction and the coloration deterioration phenomenon during the storage time.

For the exhibition of such inhibitory effects, the content of 2-mercaptobenzimidazole and/or propyl gallate can be determined as needed depending on the kind of the pressure-sensitive adhesive layer or drug, or colored degree. They are generally added in an amount of 0.01 to 5 wt. %, preferably 0.02 to 3 wt. %, more preferably 0.03 to 2 wt. % in total in the pressure-sensitive adhesive. They can be incorporated in the pressure-sensitive adhesive layer either singly or in combination.

When the total content of these 2-mercaptobenzimidazole and propyl gallate is too small, they cannot exhibit sufficient inhibitory effects and the coloration phenomenon is not prevented so much as expected. When their content is too large, on the other hand, they presumably cause interaction with other components in the pressure-sensitive adhesive layer such as crosslinking agent or with the percutaneous absorptive drug and the production of another undesirable reaction product tends to lower the stability of the preparation.

The pressure-sensitive adhesive layer of the present invention is preferably obtained by incorporating therein a percutaneous absorptive drug and 2-mercaptobenzimidazole and/or propyl gallate. Alternatively, it can be obtained by interposing the percutaneous absorptive drug as is or as a solution dissolved in an appropriate solvent between the pressure-sensitive adhesive layer and the support and then, sealing at the peripheral portion of the preparation. In this case, 2-mercaptoenzimidazole and/or propyl gallate may exist either in the drug-containing layer or pressure-sensitive adhesive layer. The decomposition of the drug during storage for days can be prevented by separating the pressure-sensitive adhesive layer into a pressure-sensitive adhesive layer portion and a drug-containing layer portion.

It is also possible to precisely control the release of the drug by inserting a microporous film between the drug-containing layer portion and the pressure-sensitive adhesive layer portion.

The thickness of the pressure-sensitive adhesive layer or the pressure-sensitive adhesive layer portion is generally from 10 to 200 μm, preferably from 15 to 150 μm.

No particular limitation is imposed on the preparation process of the percutaneous absorption preparation of the present invention. For example, it is prepared by dissolving or dispersing a pressure-sensitive adhesive, 2-mercaptobenzimidazole and/or propyl gallate and a percutaneous absorptive drug successively in a solvent, adding a known tackifier, plasticizer, absorption enhancer, surfactant and/or filler as needed, applying the resulting solution or dispersion onto at least one side of a support, and drying to form the pressure-sensitive adhesive layer on the surface of the support. Alternatively, it can be prepared by applying the above-described solution or dispersion onto a release sheet, drying the resulting sheet to form a pressure-sensitive adhesive layer on the sheet and then adhering a support to the pressure-sensitive adhesive layer.

In the percutaneous absorption preparation according to the present invention, it is possible to stack a release sheet on the surface of the pressure-sensitive adhesive layer in order to prevent the layer from sticking to a tool or container during the preparation, transport or storage or to prevent the deterioration of the preparation. Upon use, the sheet is peeled off to expose the pressure-sensitive adhesive layer surface and patched to the skin, whereby the drug is percutaneously administered.

No particular limitation is imposed on the release sheet insofar as it can be peeled easily from the pressure-sensitive adhesive layer upon use. Examples include films such as polyester, polyvinyl chloride, polyvinylidene chloride or polyethylene terephthalate and laminate films of woodfree paper or glassine paper with a polyolefin, each of which has been subjected to silicone treatment on the contact surface with the pressure-sensitive adhesive layer. The thickness of the release sheet is generally not greater than 1000 μm, preferably 30 to 200 μm.

The administration amount of the percutaneous absorption preparation according to the present invention varies depending on the kind of the percutaneous absorptive drug to be used, age, weight and symptoms of a patient and the like. In general, the preparation containing 1 to 500 mg of the percutaneous absorptive drug is patched to an adult once to seven times or so a day to the skin of 1 to 100 cm$^2$.

The present invention will hereinafter be described more specifically by examples. It should however be borne in mind that the present invention is not limited to or by these examples. Incidentally, in the following examples, all designations of part and % indicate part by weight and wt. %, respectively.

Preparation of Pressure-Sensitive Adhesive Solution A

Under an inert gas atmosphere, 60 parts of 2-ethylhexyl acrylate and 40 parts of methyl methacrylate were polymerized in ethyl acetate, whereby Pressure-sensitive adhesive solution A was prepared.

Preparation of Pressure-Sensitive Adhesive Solution B

In a similar manner to that employed for Pressure-sensitive adhesive solution A, 30 parts of butyl acrylate, 30 parts of 2-ethylhexyl acrylate and 40 parts of ethyl methacrylate were polymerized, whereby Pressure-sensitive adhesive solution B was prepared.

Preparation of Pressure-Sensitive Adhesive Solution C

In a similar manner to that employed for Pressure-sensitive adhesive solution A, 50 parts of 2-ethylhexyl acrylate, 25 parts of 2-methoxyethyl acrylate and 25 parts of vinyl acetate were polymerized, whereby Pressure-sensitive adhesive solution C. was prepared.

Preparation of Pressure-Sensitive Adhesive Solution D

Thirty parts of polyisobutylene (having a viscosity-average molecular weight of 120,000), 30 parts by polyisobutylene (having a viscosity-average molecular weight of 60,000) and 40 parts of liquid paraffin were mixed uniformly, whereby Pressure-sensitive adhesive solution D was prepared.

EXAMPLES 1 TO 15 AND COMPARATIVE EXAMPLES 1 TO 9

In each of Examples 1 to 15 and Comparative Examples 1 to 9, a pressure-sensitive adhesive solution was prepared according to the mixing ratio as shown in Table 1 and the resulting solution was applied to a separator (75 μm thick) made of polyester and dried to give a dry thickness of about 40 μm, whereby a pressure-sensitive adhesive layer was formed. The pressure-sensitive adhesive layer so formed was then stuck with a film (12 μm thick) made of polyester, whereby a percutaneous absorption preparation was obtained. Incidentally, in Table 1, 2-MBI and PGa represent 2-mercaptobenzimidazole and propyl gallate, respectively and the content means that contained in the pressure-sensitive adhesive layer after drying.

TABLE 1

|  | Adhesive | Percutaneous Absorptive Drug | Content (%) | 2MBI Content (%) | PGa Content (%) |
|---|---|---|---|---|---|
| Example 1 | A | Azelastine | 20 | 0.5 | 0.3 |
| Example 2 | A | Verapamil | 20 | 0.5 | 0.5 |
| Example 3 | A | Verapamil | 20 | 0.8 | — |
| Example 4 | B | Azelastine | 20 | 0.5 | 0.5 |
| Example 5 | B | Verapamil | 15 | 1.0 | 0.3 |
| Example 6 | B | Verapamil | 15 | — | 1.5 |
| Example 7 | B | Metoprolol | 20 | 0.5 | — |
| Example 8 | B | Metoprolol | 20 | 0.2 | 0.2 |
| Example 9 | C | Azelastine | 10 | 1.0 | — |
| Example 10 | C | Azelastine | 10 | 0.5 | 0.3 |
| Example 11 | C | Metoprolol | 15 | — | 1.0 |
| Example 12 | D | Azelastine | 15 | 1.0 | — |
| Example 13 | D | Azelastine | 20 | 1.5 | 0.5 |
| Example 14 | D | Metoprolol | 20 | 0.8 | — |
| Example 15 | D | Metoprolol | 20 | — | 1.0 |
| Comparative Example 1 | A | Azelastine | 20 | — | — |
| Comparative Example 2 | A | Verapamil | 20 | — | — |
| Comparative Example 3 | B | Azelastine | 20 | — | — |
| Comparative Example 4 | B | Verapamil | 15 | — | — |
| Comparative Example 5 | B | Metoprolol | 20 | — | — |
| Comparative Example 6 | C | Azelastine | 10 | — | — |
| Comparative Example 7 | C | Metoprolol | 15 | — | — |
| Comparative Example 8 | D | Azelastine | 15 | — | — |
| Comparative Example 9 | D | Metoprolol | 20 | — | — |

With regards to each of the percutaneous absorption preparations prepared in the above examples and comparative examples, a test of colored degree was carried out. The results are shown in Table 2.

Test on the Colored Degree of Preparation

The colored degrees of each of the percutaneous absorption preparations just after the production and after storage for one month under a hermetically sealed condition at 50° C. were studied, respectively. Each preparation was punched out into a proper size and the colored degree Δb of each preparation was measured using a calorimeter "CR-200" (manufactured by Minolta Co., Ltd.). In addition, concerning each preparation, the colored degree $Δb_o$ of the supporting tape free of the percutaneous absorptive drug, 2-mercaptobenzimidazole and/or propyl gallate was measured and it was designated as blank. From the colored degree Δb of each preparation, the colored degree $Δb_o$ was subtracted, whereby the net colored degree ($Δb - Δb_o$) of the preparation was calculated. Then, from the net colored degree of the preparation one month after storage at 50° C. under a hermetically sealed condition, the net colored degree of the preparation just after the production was subtracted, whereby an increase in the colored degree was determined.

TABLE 2

| | Net Colored Degree of Preparation ($\Delta b - \Delta b_o$) | | |
|---|---|---|---|
| | Just after Preparation | One Month after Storage at 50° C. under Hermetically Sealed Condition | Increase in Colored Degree |
| Example 1 | 0.76 | 1.24 | 0.48 |
| Example 2 | 0.31 | 0.40 | 0.09 |
| Example 3 | 0.15 | 0.22 | 0.07 |
| Example 4 | 0.09 | 0.17 | 0.08 |
| Example 5 | 0.34 | 0.49 | 0.15 |
| Example 6 | 0.68 | 0.87 | 0.19 |
| Example 7 | 1.09 | 1.48 | 0.39 |
| Example 8 | 1.62 | 1.98 | 0.36 |
| Example 9 | 0.91 | 1.24 | 0.33 |
| Example 10 | 1.06 | 1.44 | 0.38 |
| Example 11 | 0.81 | 1.06 | 0.25 |
| Example 12 | 0.72 | 0.98 | 0.26 |
| Example 13 | 1.02 | 1.24 | 0.22 |
| Example 14 | 0.48 | 0.69 | 0.21 |
| Example 15 | 0.75 | 0.93 | 0.18 |
| Comparative Example 1 | 3.56 | 5.62 | 2.06 |
| Comparative Example 2 | 1.52 | 2.21 | 0.69 |
| Comparative Example 3 | 2.54 | 4.16 | 1.62 |
| Comparative Example 4 | 3.69 | 6.24 | 2.55 |
| Comparative Example 5 | 8.46 | 10.25 | 1.79 |
| Comparative Example 6 | 6.85 | 7.98 | 1.13 |
| Comparative Example 7 | 5.28 | 6.49 | 1.21 |
| Comparative Example 8 | 4.64 | 5.92 | 1.28 |
| Comparative Example 9 | 6.16 | 8.25 | 2.09 |

Preparation of Pressure-Sensitive Adhesive Solution E

Under an inert gas atmosphere, 72 parts of 2-ethylhexyl acrylate, 25 parts of N-vinyl-2-pyrrolidone and 3 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution E was prepared.

Preparation of Pressure-Sensitive Adhesive Solution F

Under an inert gas atmosphere, 93 parts of 2-ethylhexyl acrylate and 7 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution F was prepared.

Preparation of Pressure-Sensitive Adhesive Solution G

Under an inert gas atmosphere, 50 parts of 2-ethylhexyl acrylate, 15 parts of 2-hydroxyethyl acrylate and 35 parts of vinyl acetate were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution G was prepared.

Preparation of Pressure-Sensitive Adhesive Solution H

Under an inert gas atmosphere, 75 parts of 2-ethylhexyl acrylate, 20 parts of butyl acrylate and 5 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution H was prepared.

Preparation of Pressure-Sensitive Adhesive Solution J

Under an inert gas atmosphere, 95 parts of 2-ethylhexyl acrylate and 5 parts of 2-hydroxyethyl acrylate were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution J was prepared.

Preparation of Pressure-Sensitive Adhesive Solution K

Under an inert gas atmosphere, 98 parts of 2-ethylhexyl acrylate and 2 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution K was prepared.

Preparation of Pressure-Sensitive Adhesive Solution L

Under an inert gas atmosphere, 75 parts of 2-ethylhexyl acrylate, 23 parts of butyl acrylate and 2 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution L was prepared.

Preparation of Pressure-Sensitive Adhesive Solution M

Under an inert gas atmosphere, 80 parts of 2-ethylhexyl acrylate, 19 parts of N-vinyl-2-pyrrolidone and 1 part of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution M was prepared.

EXAMPLES 16 TO 34 AND COMPARATIVE EXAMPLES 10 TO 21

In each of Examples 16 to 34 and Comparative Examples 10 to 21, a pressure-sensitive adhesive solution containing a drug was prepared and the resulting solution was applied to a separator (75 μm thick) made of polyester and dried to give a dry thickness of about 60 μm, whereby a pressure-sensitive adhesive layer was formed. The pressure-sensitive adhesive layer so formed was then stuck with a film (12 μm thick) made of polyester, whereby a percutaneous absorption preparation was obtained. Incidentally, in Table 3, 2-MBI, PGa and IPM represent 2-mercaptobenzimidazole, propyl gallate and isopropyl myristate, respectively and the content means that in the pressure-sensitive adhesive layer after drying.

TABLE 3

| | Adhesive | Percutaneous Absorptive Drug (%) | | Additive (%) | | 2MBI Content (%) | PGa Content (%) |
|---|---|---|---|---|---|---|---|
| Example 16 | E | Azelastine | 25 | — | | 0.5 | 0.5 |
| Example 17 | E | Metoprolol | 20 | IPM | 50 | 0.3 | 0.2 |
| Example 18 | F | Verapamil | 30 | — | | 0.5 | 0.5 |
| Example 19 | F | Verapamil | 25 | — | | 1.0 | — |
| Example 20 | F | Verapamil | 25 | — | | — | 1.0 |
| Example 21 | F | Metoprolol | 25 | IPM | 45 | 0.3 | 0.2 |
| Example 22 | G | Azelastine | 15 | — | | 0.6 | 0.5 |
| Example 23 | G | Metoprolol | 15 | — | | 0.5 | 1.0 |
| Example 24 | H | Verapamil | 20 | — | | 0.5 | — |
| Example 25 | H | Verapamil | 20 | — | | — | 0.5 |
| Example 26 | H | Azelastine | 25 | — | | 0.5 | 1.0 |
| Example 27 | H | Metoprolol | 25 | — | | 0.6 | 0.4 |
| Example 28 | J | Azelastine | 15 | — | | 0.8 | — |
| Example 29 | J | Azelastine | 15 | — | | — | 0.8 |
| Example 30 | J | Metoprolol | 20 | — | | 0.5 | 0.3 |
| Example 31 | J | Metoprolol | 20 | IPM | 40 | 0.3 | 0.2 |
| Example 32 | K | Azelastine | 20 | — | | 0.5 | 0.5 |
| Example 33 | L | Verapamil | 25 | — | | 0.8 | — |
| Example 34 | M | Propranolol | 25 | — | | 0.3 | 0.2 |
| Comparative Example 10 | E | Azelastine | 25 | — | | — | — |
| Comparative Example 11 | E | Metoprolol | 20 | IPM | 50 | — | — |
| Comparative Example 12 | F | Verapamil | 30 | — | | — | — |
| Comparative Example 13 | F | Metoprolol | 25 | IPM | 45 | — | — |
| Comparative Example 14 | G | Azelastine | 15 | — | | — | — |
| Comparative Example 15 | G | Metoprolol | 15 | — | | — | — |
| Comparative Example 16 | H | Verapamil | 20 | — | | — | — |
| Comparative Example 17 | H | Azelastine | 25 | — | | — | — |
| Comparative Example 18 | H | Metoprolol | 25 | — | | — | — |
| Comparative Example 19 | J | Azelastine | 15 | — | | — | — |
| Comparative Example 20 | J | Metoprolol | 20 | — | | — | — |
| Comparative Example 21 | J | Metoprolol | 20 | IPM | 40 | — | — |

With regards to each of the percutaneous absorptive preparations produced in the above examples and comparative examples, the colored degree of the preparation and stability of the drug content were tested in accordance with the methods as described below. The results are shown in Table 4.

Test on the Colored Degree of Preparation

The colored degrees of each of the percutaneous absorption preparations just after the production and after storage for two months under a hermetically sealed condition at 50° C. were studied, respectively. Each preparation was punched out into a proper size and the colored degree $\Delta b$ of each preparation was measured using a calorimeter "CR-200" (manufactured by Minolta). In addition, concerning each preparation, the colored degree $\Delta b_o$ of the support tape free of the percutaneous absorptive drug, 2-mercaptobenzimidazole and/or propyl gallate was measured and it was designated as blank. From the colored degree $\Delta b$ of each preparation, the colored degree $\Delta b_o$ was subtracted, whereby the net colored degree ($\Delta b - \Delta b_o$) of the preparation was calculated. Then, from the net colored degree of the preparation two months after storage at 50° C. under a hermetically sealed condition, the net colored degree just after the preparation was subtracted, whereby an increase in the colored degree was determined.

Test on Stability of Drug Content in Preparation

Concerning each of the percutaneous absorption preparations, stability of the drug content in each preparation which had been stored for two months at 50° C. under a hermetically sealed condition was investigated. Each preparation was punched out into a proper size, followed by extraction under shaking. The drug content in the extracted solution was thereafter measured by a high-performance liquid chromatography.

TABLE 4

| | Colored Degree of Preparation ($\Delta b - \Delta b_o$) | | Increase in Colored Degree | Stability of Drug Content after Stored for 2 Months at 50° C. under Hermetically Sealed Condition (relative to initial value %) |
|---|---|---|---|---|
| | Just after Preparation | After Storage | | |
| Example 16 | 1.06 | 1.34 | 0.28 | 99.6 |
| Example 17 | 0.84 | 1.02 | 0.18 | 99.0 |
| Example 18 | 1.86 | 2.08 | 0.22 | 98.2 |
| Example 19 | 1.25 | 1.46 | 0.21 | 98.0 |
| Example 20 | 1.36 | 1.54 | 0.18 | 98.4 |
| Example 21 | 0.75 | 0.98 | 0.23 | 99.4 |
| Example 22 | 2.48 | 3.52 | 1.04 | 97.0 |
| Example 23 | 1.86 | 2.39 | 0.53 | 98.5 |
| Example 24 | 1.46 | 2.05 | 0.59 | 98.7 |
| Example 25 | 1.58 | 2.09 | 0.51 | 99.2 |
| Example 26 | 1.68 | 2.37 | 0.69 | 98.0 |
| Example 27 | 1.85 | 2.24 | 0.39 | 98.4 |
| Example 28 | 2.18 | 2.56 | 0.38 | 97.8 |
| Example 29 | 1.76 | 2.15 | 0.39 | 99.0 |
| Example 30 | 1.78 | 2.34 | 0.56 | 98.1 |
| Example 31 | 1.56 | 1.87 | 0.31 | 98.3 |
| Example 32 | 0.34 | 1.89 | 1.55 | 98.4 |
| Example 33 | 0.68 | 2.57 | 1.89 | 99.2 |
| Example 34 | 0.92 | 2.46 | 1.54 | 98.8 |
| Comparative Example 10 | 4.52 | 6.28 | 1.76 | 96.3 |
| Comparative Example 11 | 3.27 | 4.56 | 1.29 | 96.8 |
| Comparative Example 12 | 6.29 | 9.56 | 3.27 | 95.7 |
| Comparative Example 13 | 5.84 | 8.43 | 2.59 | 95.9 |
| Comparative Example 14 | 10.64 | 20.62 | 9.98 | 95.0 |
| Comparative Example 15 | 13.58 | 27.41 | 13.83 | 94.6 |
| Comparative Example 16 | 7.51 | 10.34 | 2.83 | 96.1 |
| Comparative Example 17 | 5.26 | 6.94 | 1.68 | 97.0 |
| Comparative Example 18 | 6.84 | 12.56 | 5.72 | 95.5 |
| Comparative Example 19 | 21.62 | 35.48 | 13.86 | 94.5 |
| Comparative Example 20 | 24.56 | 40.85 | 16.29 | 93.5 |
| Comparative Example 21 | 17.24 | 29.46 | 12.22 | 95.2 |

Preparation of Pressure-Sensitive Adhesive Solution N

Under an inert gas atmosphere, 90 parts of 2-ethylhexyl acrylate and 10 parts of 2-hydroxyethyl acrylate were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution N was prepared.

Preparation of Pressure-Sensitive Adhesive Solution P

Under an inert gas atmosphere, 95 parts of 2-ethylhexyl acrylate and 5 parts of acrylic acid were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution P was prepared.

Preparation of Pressure-Sensitive Adhesive Solution O

Under an inert gas atmosphere, 70 parts of 2-ethylhexyl acrylate, 20 parts of butyl acrylate and 10 parts of acrylic acid were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution Q was prepared.

Preparation of Pressure-Sensitive Adhesive Solution R

Under an inert gas atmosphere, 70 parts of 2-ethylhexyl acrylate, 25 parts of N-vinyl-2-pyrrolidone and 5 parts of acrylic acid were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution R was prepared.

Preparation of Pressure-Sensitive Adhesive Solution S

Under an inert gas atmosphere, 60 parts of 2-ethylhexyl acrylate, 10 parts of 2-hydroxyethyl acrylate and 30 parts of vinyl acetate were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution S was prepared.

Preparation of Pressure-Sensitive Adhesive Solution T

Under an inert gas atmosphere, 85 parts of 2-ethylhexyl acrylate and 15 parts of 2-hydroxyethyl acrylate were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution T was prepared.

Preparation of Pressure-Sensitive Adhesive Solution U

Under an inert gas atmosphere, 70 parts of 2-ethylhexyl acrylate, 23 parts of N-vinyl-2-pyrrolidone and 7 parts of acrylic acid were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution U was prepared.

Preparation of Pressure-Sensitive Adhesive Solution V

Under an inert gas atmosphere, 97 parts of 2-ethylhexyl acrylate and 3 parts of acrylic acid were charged in a flask, followed by the addition of 0.2 part of benzoyl peroxide as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution V was prepared.

Preparation of Pressure-Sensitive Adhesive Solution W

Under an inert gas atmosphere, 98 parts of 2-ethylhexyl acrylate and 2 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution W was prepared.

Preparation of Pressure-Sensitive Adhesive Solution X

Under an inert gas atmosphere, 75 parts of 2-ethylhexyl acrylate, 23 parts of butyl acrylate and 2 parts of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution X was prepared.

Preparation of Pressure-Sensitive Adhesive Solution Y

Under an inert gas atmosphere, 80 parts of 2-ethylhexyl acrylate, 19 parts of N-vinyl-2-pyrrolidone and 1 part of acrylic acid were charged in a flask, followed by the addition of 0.3 part of azobisisobutylonitrile as a polymerization initiator, whereby polymerization was started. The polymerization reaction was effected at a temperature which had been controlled to 58 to 62° C. by the adjustment of the stirring rate and external bath temperature and dropwise addition of ethyl acetate, whereby Pressure-sensitive adhesive solution Y was prepared.

EXAMPLES 35 TO 50 AND COMPARATIVE EXAMPLES 22 to 35

In each of Examples 35 to 50 and Comparative Examples 22 to 35, a pressure-sensitive adhesive solution containing a drug was prepared at the mixing ratio as shown in Table 5 and the resulting solution was applied to a separator (75 μm thick) made of polyester and dried to give a dry thickness of about 60 μm, whereby a pressure-sensitive adhesive layer was formed. The pressure-sensitive adhesive layer so obtained was then stuck with a film (12 μm thick) made of polyester, whereby a percutaneous absorption preparation was obtained. Incidentally, in Table 5, 2-MBI, PGa and IPM represent 2-mercaptobenzimidazole, propyl gallate and isopropyl myristate, respectively and the content means that in the pressure-sensitive adhesive layer after drying.

TABLE 5

| | Adhesive | Percutaneous Absorptive Drug (%) | | Additive (%) | | 2MBI Content (%) | PGa Content (%) |
|---|---|---|---|---|---|---|---|
| Example 35 | N | Verapamil | 20 | — | | 0.6 | 0.4 |
| Example 36 | N | Azelastine | 20 | IPM | 40 | 0.5 | — |
| Example 37 | N | Azelastine | 20 | IPM | 40 | — | 0.7 |
| Example 38 | P | Azelastine | 25 | — | | 0.5 | 0.3 |
| Example 39 | P | Azelastine | 20 | — | | 0.8 | — |
| Example 40 | P | Propranolol | 30 | IPM | 40 | 0.3 | 0.2 |
| Example 41 | Q | Verapamil | 25 | — | | 0.5 | — |
| Example 42 | Q | Verapamil | 25 | — | | — | 0.7 |
| Example 43 | Q | Propranolol | 25 | — | | 0.5 | 0.5 |
| Example 44 | R | Verapamil | 20 | — | | 0.5 | 0.5 |
| Example 45 | R | Propranolol | 25 | IPM | 45 | 0.2 | 0.2 |
| Example 46 | S | Verapamil | 20 | — | | 0.6 | 0.4 |
| Example 47 | S | Propranolol | 20 | — | | 0.5 | 1.0 |
| Example 48 | T | Azelastine | 15 | — | | 0.2 | 0.2 |
| Example 49 | U | Verapamil | 20 | — | | 0.2 | 0.2 |
| Example 50 | V | Metoprolol | 20 | — | | 0.2 | 0.2 |
| Comparative Example 22 | N | Verapamil | 20 | — | | — | — |
| Comparative Example 23 | N | Azelastine | 20 | IPM | 40 | — | — |
| Comparative Example 24 | P | Azelastine | 25 | — | | — | — |
| Comparative Example 25 | P | Azelastine | 20 | — | | — | — |
| Comparative Example 26 | P | Propranolol | 30 | IPM | 40 | — | — |
| Comparative Example 27 | Q | Verapamil | 25 | — | | — | — |
| Comparative Example 28 | Q | Propranolol | 25 | — | | — | — |
| Comparative Example 29 | R | Verapamil | 20 | — | | — | — |
| Comparative Example 30 | R | Propranolol | 25 | IPM | 45 | — | — |
| Comparative Example 31 | S | Verapamil | 20 | — | | — | — |
| Comparative Example 32 | S | Propranolol | 20 | — | | — | — |
| Comparative Example 33 | W | Azelastine | 20 | — | | 0.5 | 0.5 |
| Comparative Example 34 | X | Verapamil | 25 | — | | 0.8 | — |
| Comparative Example 35 | Y | Propranolol | 25 | — | | 0.3 | 0.2 |

With regards to each of the percutaneous absorptive preparations produced in the above examples and comparative examples, the colored degree and stability of the drug content were tested in accordance with the manner as described above. The results are shown in Table 6.

TABLE 6

| | Colored Degree of Preparation ($\Delta b - \Delta b_o$) | | Increase in Colored Degree | Stability of Drug Content after Stored for 2 Months at 50° C. under Hermetically Sealed Condition (relative to initial value %) |
|---|---|---|---|---|
| | Just after Preparation | After Storage | | |
| Example 35 | 2.45 | 3.26 | 0.81 | 99.4 |
| Example 36 | 1.95 | 2.78 | 0.83 | 99.2 |
| Example 37 | 2.13 | 2.86 | 0.73 | 98.6 |
| Example 38 | 2.04 | 2.56 | 0.52 | 99.0 |
| Example 39 | 1.68 | 2.14 | 0.46 | 98.2 |
| Example 40 | 1.46 | 1.89 | 0.43 | 99.5 |
| Example 41 | 1.25 | 1.71 | 0.46 | 98.8 |
| Example 42 | 1.75 | 2.20 | 0.45 | 98.4 |
| Example 43 | 1.68 | 2.14 | 0.46 | 98.2 |
| Example 44 | 1.86 | 2.35 | 0.49 | 99.6 |
| Example 45 | 1.25 | 1.71 | 0.46 | 100.0 |
| Example 46 | 2.23 | 2.79 | 0.56 | 97.8 |
| Example 47 | 1.96 | 2.45 | 0.49 | 98.0 |
| Example 48 | 2.56 | 2.78 | 0.22 | 99.2 |
| Example 49 | 1.28 | 1.49 | 0.21 | 98.4 |
| Example 50 | 1.14 | 1.32 | 0.18 | 98.1 |
| Comparative Example 22 | 22.56 | 35.19 | 12.63 | 94.2 |
| Comparative Example 23 | 25.86 | 45.24 | 19.38 | 93.5 |
| Comparative Example 24 | 8.56 | 11.23 | 2.67 | 93.1 |
| Comparative Example 25 | 7.94 | 10.56 | 2.62 | 94.6 |
| Comparative Example 26 | 6.14 | 9.43 | 3.29 | 95.0 |
| Comparative Example 27 | 5.28 | 12.56 | 7.28 | 92.5 |
| Comparative Example 28 | 6.41 | 13.58 | 7.17 | 93.6 |
| Comparative Example 29 | 7.25 | 11.86 | 4.61 | 94.5 |
| Comparative Example 30 | 4.56 | 7.28 | 2.72 | 93.0 |
| Comparative Example 31 | 10.41 | 18.56 | 8.15 | 94.1 |
| Comparative Example 32 | 9.31 | 15.27 | 5.96 | 95.6 |
| Comparative Example 33 | 0.34 | 1.89 | 1.55 | 98.4 |
| Comparative Example 34 | 0.68 | 2.57 | 1.89 | 99.2 |
| Comparative Example 35 | 0.92 | 2.46 | 1.54 | 98.8 |

While the invention has been described in detail and with reference to specific embodiments thereof, it will be apparent to one skilled in the art that various changes and modifications can be made therein without departing from the spirit and scope thereof.

What is claimed is:

1. A percutaneous absorption preparation which comprises a support and a pressure-sensitive adhesive layer formed on at least one side of the support, wherein the pressure-sensitive adhesive layer contains a percutaneous absorptive drug and 2-mercaptobenzimidazole, with the proviso that the percutaneous absorptive drug is not 6-amino-5-chloro-1-isopropyl-2-(4-methyl-1-1-piperazinyl) benzimidazole and pharmacologically acceptable salts thereof.

2. The percutaneous absorption preparation of claim 1, wherein said pressure-sensitive adhesive layer is formed of a non-functional pressure-sensitive adhesive.

3. The percutaneous absorption preparation of claim 2, wherein said non-functional pressure-sensitive adhesive is at least one pressure-sensitive adhesive selected from the group consisting of pressure-sensitive adhesives made of an acrylic polymer, rubber pressure-sensitive adhesives, silicone pressure-sensitive adhesives, vinyl ether pressure-sensitive adhesives and vinyl ester pressure-sensitive adhesives.

4. The percutaneous absorption preparation of claim 1, wherein said pressure-sensitive adhesive layer comprises an acrylic polymer obtained by copolymerization of a functional monomer as an essential component.

5. The percutaneous absorption preparation of claim 4, wherein an azo compound is employed as a polymerization initiator upon copolymerization to obtain the acrylic polymer.

6. The percutaneous absorption preparation of claim 4, wherein an organic peroxide compound is used as a polymerization initiator upon copolymerization to obtain the acrylic polymer.

* * * * *